(12) United States Patent
Pogorelsky

(10) Patent No.: US 8,419,430 B2
(45) Date of Patent: Apr. 16, 2013

(54) SYSTEM AND METHOD FOR INCREMENTALLY MOVING TEETH

(76) Inventor: Yan Pogorelsky, Miller Place, NY (US)

(*) Notice: Subject to any disclaimer, the term of this patent is extended or adjusted under 35 U.S.C. 154(b) by 0 days.

(21) Appl. No.: 13/078,965

(22) Filed: Apr. 2, 2011

(65) Prior Publication Data

US 2011/0236849 A1   Sep. 29, 2011

(51) Int. Cl.
*A61C 13/10* (2006.01)

(52) U.S. Cl.
USPC .............................. 433/193; 433/74; 433/213

(58) Field of Classification Search ..................... 433/53, 433/74, 176, 193, 213, 223
See application file for complete search history.

(56) References Cited

U.S. PATENT DOCUMENTS

| | | | |
|---|---|---|---|
| 1,780,117 A * | 10/1930 | Craigo | ............................ 433/74 |
| 3,153,283 A | 10/1964 | Weissman | |
| 4,060,899 A | 12/1977 | Sauter | |
| 4,371,340 A | 2/1983 | Imaizumi | |
| 4,767,331 A * | 8/1988 | Hoe | ............................. 433/213 |
| 4,801,264 A | 1/1989 | Weissman | |
| 5,286,191 A | 2/1994 | Poveromo | |
| 5,752,831 A | 5/1998 | Padros-Frader | |
| 5,788,489 A | 8/1998 | Huffman | |
| 5,788,494 A | 8/1998 | Phimmasone | |
| 5,975,893 A | 11/1999 | Chishti | |
| 6,217,325 B1 | 4/2001 | Chishti | |
| 6,299,440 B1 | 10/2001 | Phan | |
| 6,318,994 B1 | 11/2001 | Chishti | |
| 6,390,812 B1 | 5/2002 | Chishti | |
| 6,394,801 B2 | 5/2002 | Chishti | |
| 6,398,548 B1 | 6/2002 | Muhammad | |
| 6,406,292 B1 | 6/2002 | Chishti | |
| 6,450,807 B1 | 9/2002 | Chishti | |
| 6,457,972 B1 | 10/2002 | Chishti | |
| 6,471,511 B1 | 10/2002 | Chishti | |
| 6,485,298 B2 | 11/2002 | Chishti | |

(Continued)

FOREIGN PATENT DOCUMENTS

| KR | 10-2002-0080305 | 10/2002 |
|---|---|---|
| RU | 2223716 | 2/2004 |

OTHER PUBLICATIONS

O.I. Arsenina et al. Diagnostics and planning of orthodontic treatment of patients with crowded teeth position with the use of elastomeric correction splints. Stomatologiia (Mosk) 2011; 2:78.

(Continued)

*Primary Examiner* — Cris L Rodriguez
*Assistant Examiner* — Eric Rosen
(74) *Attorney, Agent, or Firm* — Leason Ellis LLP

(57) ABSTRACT

A dental model kit includes a set of dowel pins for successive use with at least one tooth die that is part of the dental model kit. Each dowel pin includes an upstanding tooth anchor section that is configured to be fixedly attached to the tooth die; and a main body section having a top surface from which the tooth anchor section extends. The main body section is for reception within a base of the dental model kit. According to the present invention, a location of the tooth anchor section relative to the top surface changes from an initial position associated with an initial pin that is part of the set to a final position associated with a final pin that is part. Successive movement of the tooth anchor section is translated into successive movement of the tooth die both in a desired direction and a desired distance.

18 Claims, 7 Drawing Sheets

U.S. PATENT DOCUMENTS

| | | |
|---|---|---|
| 6,499,997 B2 | 12/2002 | Chishti et al. |
| 6,554,611 B2 | 4/2003 | Chishti |
| 6,582,227 B2 | 6/2003 | Phan |
| 6,602,070 B2 | 8/2003 | Miller |
| 6,626,666 B2 | 9/2003 | Chishti |
| 6,629,840 B2 | 10/2003 | Chishti |
| 6,685,469 B2 | 2/2004 | Chishti |
| 6,699,037 B2 | 3/2004 | Chishti |
| 6,705,861 B2 | 3/2004 | Chishti |
| 6,722,880 B2 | 4/2004 | Chishti |
| 6,729,876 B2 | 5/2004 | Chishti |
| 6,761,560 B2 | 7/2004 | Miller |
| 6,767,208 B2 | 7/2004 | Kaza |
| 6,783,360 B2 | 8/2004 | Chishti |
| 6,786,721 B2 | 9/2004 | Chishti |
| 6,802,713 B1 | 10/2004 | Chishti |
| 7,037,108 B2 | 5/2006 | Chishti |
| 7,037,111 B2 | 5/2006 | Miller |
| 7,063,533 B2 | 6/2006 | Phan |
| 7,074,038 B1 | 7/2006 | Miller |
| 7,077,647 B2 | 7/2006 | Choi |
| 7,108,508 B2 | 9/2006 | Hedge |
| 7,156,661 B2 | 1/2007 | Choi |
| 7,192,275 B2 | 3/2007 | Miller |
| 7,220,122 B2 | 5/2007 | Chishti |
| 7,247,021 B2 | 7/2007 | Jones |
| 7,261,533 B2 | 8/2007 | Wrosz |
| 7,273,367 B2 | 9/2007 | Huges |
| 7,293,988 B2 | 11/2007 | Wen |
| 7,326,051 B2 | 2/2008 | Miller |
| 7,331,783 B2 | 2/2008 | Chishti |
| 7,335,024 B2 | 2/2008 | Wen |
| 7,377,778 B2 | 5/2008 | Chishti |
| 7,435,083 B2 | 10/2008 | Chishti |
| 7,476,100 B2 | 1/2009 | Kuo |
| 7,578,674 B2 | 8/2009 | Chishti |
| 7,600,999 B2 | 10/2009 | Knopp |
| 2002/0094503 A1 | 7/2002 | Chishti |
| 2003/0207227 A1 | 11/2003 | Abolfathi |
| 2003/0211440 A1 | 11/2003 | Kuo |
| 2004/0019723 A1 | 1/2004 | Ostrovsky et al. |
| 2004/0166456 A1 | 8/2004 | Chishti |
| 2004/0166462 A1 | 8/2004 | Phan |
| 2004/0166463 A1 | 8/2004 | Wen et al. |
| 2004/0170941 A1 | 9/2004 | Phan |
| 2004/0202983 A1 | 10/2004 | Tricca |
| 2004/0243361 A1 | 12/2004 | Steuben |
| 2005/0055118 A1 | 3/2005 | Nikolskiy |
| 2005/0106525 A1 | 5/2005 | Knopp |
| 2005/0233278 A1 | 10/2005 | Kim |
| 2005/0244782 A1 | 11/2005 | Chishti |
| 2006/0003283 A1 | 1/2006 | Miller |
| 2006/0084030 A1 | 4/2006 | Phan |
| 2006/0222474 A1 | 10/2006 | Brown et al. |
| 2007/0015105 A1 | 1/2007 | Campanello |
| 2007/0065771 A1 | 3/2007 | Kohani |
| 2007/0092850 A1 | 4/2007 | Kaza |
| 2008/0020337 A1 | 1/2008 | Phan |
| 2008/0020340 A1 | 1/2008 | Matov |
| 2008/0166676 A1 | 7/2008 | Chishti |
| 2008/0182221 A1 | 7/2008 | Chishti |
| 2008/0187879 A1 | 8/2008 | Chishti |
| 2008/0280258 A1 | 11/2008 | Wen |
| 2009/0298017 A1* | 12/2009 | Boerjes et al. ............... 433/214 |
| 2010/0151404 A1 | 6/2010 | Wu |
| 2011/0104639 A1 | 5/2011 | Pogorelsky |
| 2011/0104640 A1 | 5/2011 | Pogorelsky |

OTHER PUBLICATIONS

Altan Varol et al. The role of computer-aided 3D surgery and stereolithographic modelling for vector orientation in premaxillary and trans-sinusoidal maxillary distraction osteogenesis. Int J Med Robotics Compr Assist Surg 2009; 5:198-206.

* cited by examiner

SYSTEM AND METHOD FOR INCREMENTALLY MOVING TEETH

TECHNICAL FIELD

The present invention relates to orthodontics and in particular, the present invention relates to a system and method for incrementally moving one or more teeth from an initial tooth arrangement to a final tooth arrangement.

BACKGROUND

Orthodontics is a specialty of dentistry that is concerned with the study and treatment of malocclusions (improper bites) which can be a result of tooth irregularity, disproportionate jaw relationships, or both. Orthodontic treatment can focus on dental displacement only and can be carried out for purely aesthetic reasons with regard to improving the general appearance of patient's teeth. However, there are other orthodontic treatments that are more complex and are needed to reconstruct the face. This type of treatment is most often prescribed for practical reasons such as providing the patient with a functionally improved bite (occlusion).

Conventionally, repositioning teeth for aesthetic reasons or other reasons is accomplished by wearing a device that is commonly referred as dental braces. Dental braces are formed of a variety of appliances such as brackets, archwires, ligatures, and O-rings. Attaching dental braces to the teeth of a patient is a tedious, time consuming task that requires a number of meetings between the patient and orthodontist to first prepare and fit the dental braces and then make necessary adjustments to the dental braces. Before the braces are fixedly attached to the patient's teeth, various molds and fittings are required in order to formulate the strategy. To attach the braces, a weak acid is first applied to the teeth to increase the adherence of the braces to the teeth. Brackets and bands that form the dental braces are bonded to the patient's teeth using cement.

The primary force-inducing appliance in a conventional set of braces is the archwire. The archwire is resilient and is attached to the brackets by way of slots in the brackets. The archwire links the brackets together and exerts forces on them to move the teeth over time. After the archwire is in place, periodic meetings with the orthodontist are required and during these meetings, the patient's braces are adjusted by installing a different archwire having different force-inducing properties or by replacing of tightening existing ligatures.

Besides being a time consuming process, conventional braces are also very unsightly and are uncomfortable to wear to the presence of these components in the mouth, bonded to and extending across the teeth, etc.

The physical 3-D model of the patient's teeth allows the orthodontist to individually adjust those tooth dies that require adjustment as part of the treatment plan. The model is used in combination with conventional dentist equipment (e.g., vacuum forming equipment) to construct aligners that are used to adjust the patient's tooth in an incremental manner from an initial tooth arrangement to a desired, final tooth arrangement. The present system provides a number of advantages and a degree of customization not available with the conventional computer-based systems.

SUMMARY

According to one embodiment, a dental model kit includes a set of dowel pins for successive use with at least one tooth die that is part of the dental model kit. Each dowel pin includes an upstanding tooth anchor section that is configured to be fixedly attached to the tooth die; and a main body section having a top surface from which the tooth anchor section extends. The main body section is for reception within a base of the dental model kit. According to the present invention, a location of the tooth anchor section relative to the top surface changes from an initial position associated with an initial pin that is part of the set to a final position associated with a final pin that is part. Successive movement of the tooth anchor section is translated into successive movement of the tooth die both in a desired direction and a desired distance.

A method for incrementally adjusting a position of at least one tooth includes the steps of: (1) providing a physical 3-D tooth die model that includes: a first model part that is formed of a plurality of tooth dies; a second model part complementary to the first model part and being in the form of a base that supports the tooth dies; and a set of dowel pins, each dowel pin for use with the tooth die that is intended to be incrementally moved; (2) coupling an initial dowel pin with the tooth die that is intended to be incrementally moved and with the base, the initial dowel pin having an upstanding tooth anchor section extending from a main pin body, the tooth anchor section being in a first location; (3) casting a first aligner, using the tooth die model, for wearing over teeth of the patient; (4) using successively a set of dowel pins in which a location of the tooth anchor section relative to the main pin body changes so as to cause a change in position of the corresponding tooth die relative to the base, wherein in a final down pin, the tooth anchor section is in a final position that positions the tooth die in a desired final location that also corresponds to a target location of the tooth of the patient; and (5) successively casting a plurality of aligners using successive tooth die models that include the set of dowel pins in which the locations of the tooth anchor sections vary so as to effectuate an incremental change in the location of the tooth of the patient.

These and other aspects, features and advantages shall be apparent from the accompanying Drawings and description of certain embodiments of the invention.

DETAILED DESCRIPTION OF CERTAIN EMBODIMENTS OF THE INVENTION

In accordance with one embodiment of the present invention, systems and methods are provided for incrementally moving one or more teeth using a plurality of discrete members (aligners) that successively move one or more teeth by predetermined amounts. The system is configured so that the tooth movements are those normally associated with orthodontic treatment, including translation in all three orthogonal directions relative to a vertical centerline, rotation of the tooth centerline in the two orthodontic directions ("root angulation" and "torque"), as well as rotation about the centerline. These movements are shown in FIG. 1.

As described herein and in contrast to the computer-based systems of the conventional systems described above, the system and method of the present invention avoid the complexity of the computer-based systems and provide a more personal treatment plan that can be discussed and developed directly between the patient and his or her orthodontist. The present invention generally is in the form of an adjustable dowel pin assembly that support tooth dies and are embedded into a physical 3-D model of the patient's teeth to allow the orthodontist to individually adjust those tooth dies that require adjustment as part of the treatment plan. The model is used in combination with conventional dentist equipment (e.g., vacuum forming equipment) to construct aligners that are used to adjust the patient's tooth in an incremental manner from an initial tooth arrangement to a desired, final tooth arrangement. The present system provides a number of advantages and a degree of customization not available with the conventional computer-based systems.

Figure 1:
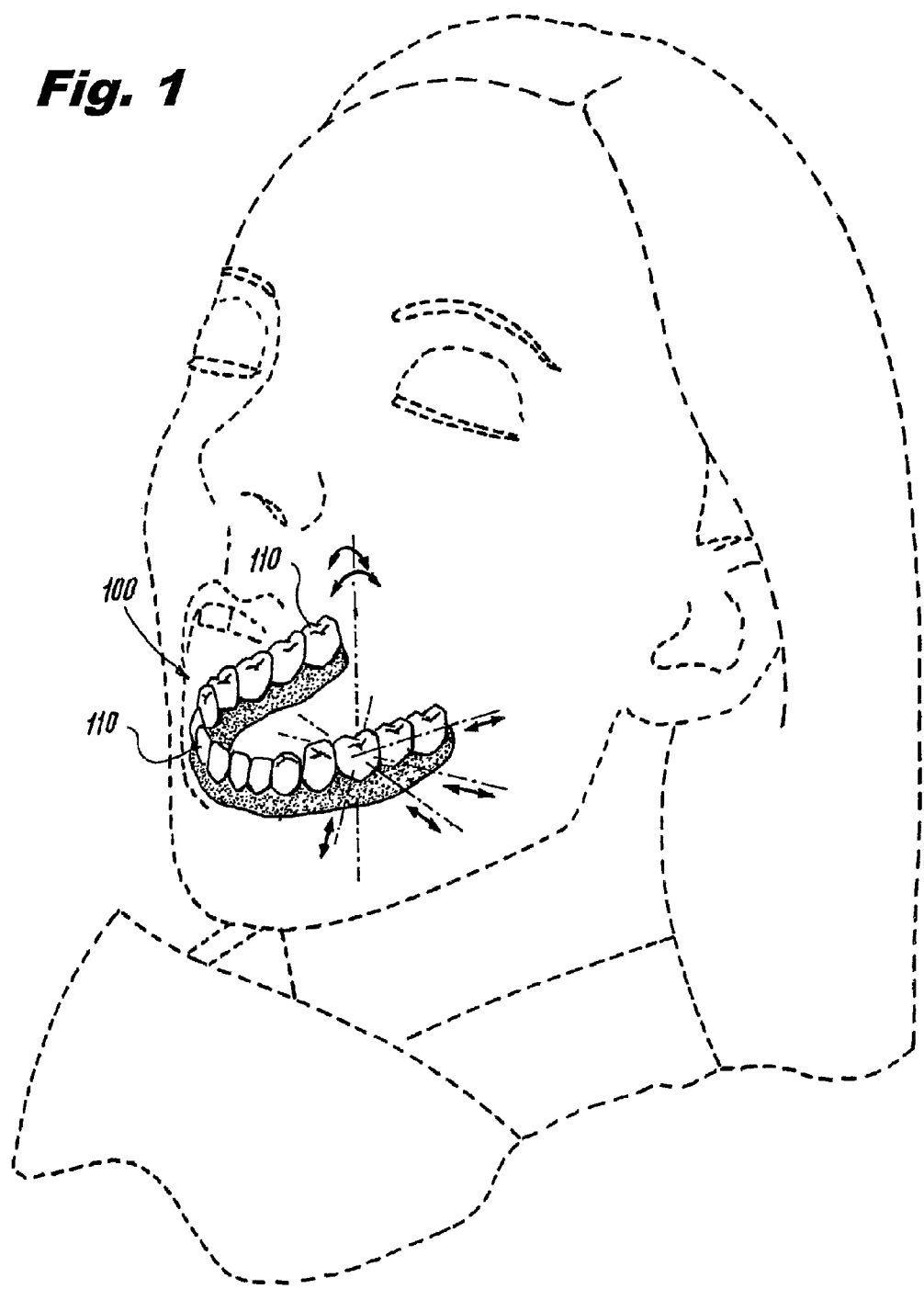
FIG. 1 illustrates a patient's jaw and provides a general indication of how teeth can be moved in accordance with the system and method of the present invention.

FIG. 1 shows a representative jaw 100 that includes sixteen teeth 110. The present invention is intended to move at least some of these teeth 110 from an initial tooth arrangement to a final tooth arrangement.

Figure 2:
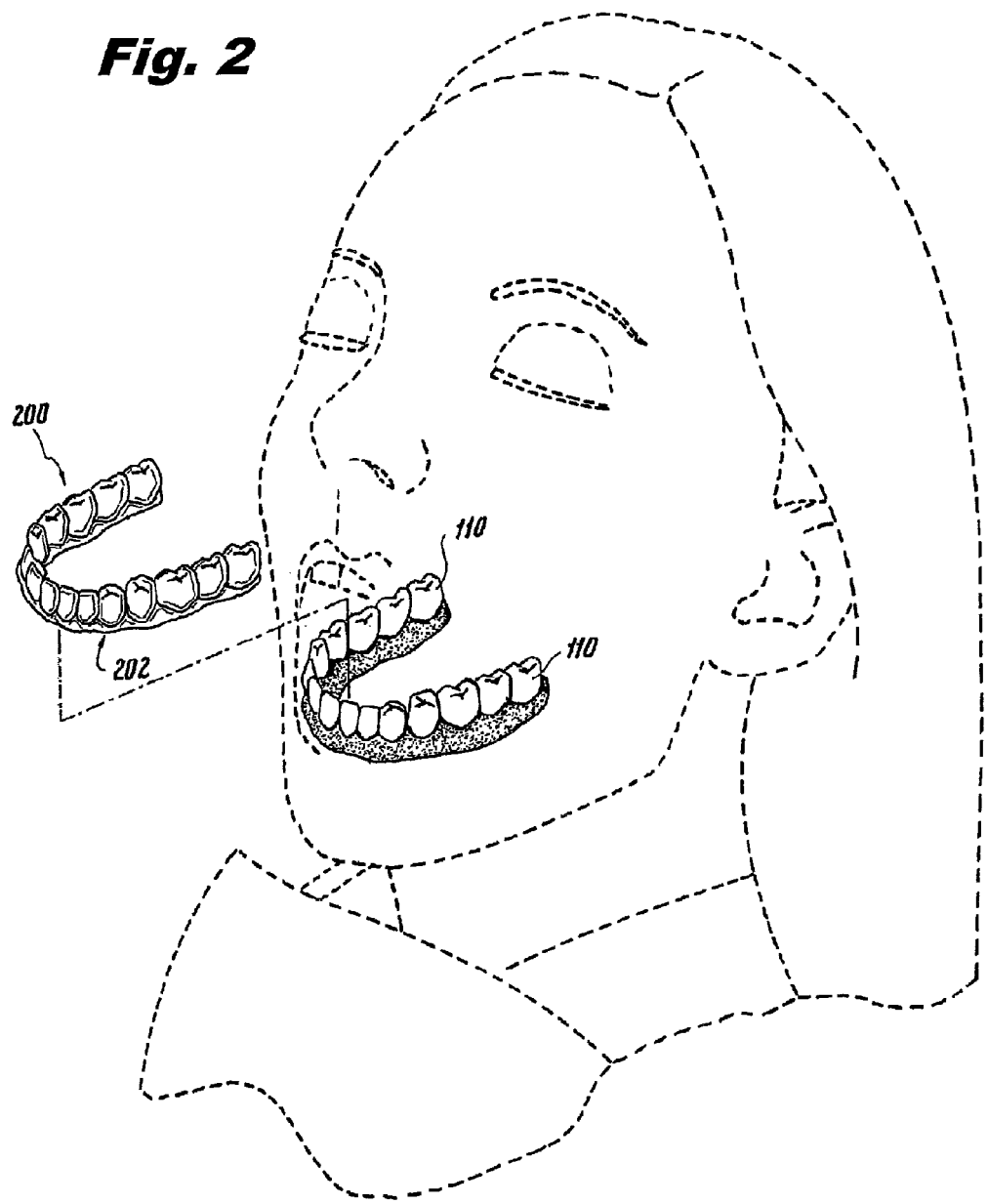
FIG. 2 illustrates the jaw of FIG. 1 with an incremental position adjustment device (aligner) that has been configured for placement over the teeth to cause over time incremental movement of the teeth.

FIG. 2 is a perspective view of a discrete member or apparatus (teeth positioner or aligner) 200 that is part of the system of the present invention and is intended to cause the movement of one or more teeth 110. In order to move the one or more target teeth from the initial tooth arrangement to the final tooth arrangement, one to a plurality of aligners 200 are used over a prescribed period of time determined by the orthodontist. Each aligner is intended to effect incremental repositioning of individual teeth in the jaw as described above. When plural aligners 200 are created for a given patient, they are intended to be worn successively by the patient in order to achieve gradual tooth repositioning as described below in greater detail. An exemplary aligner 200 is formed of a polymeric shell that has a cavity 202 shaped to receive and resiliently reposition teeth from one tooth arrangement to a successive tooth arrangement. Typically, the polymeric shell fits over all teeth present in the upper or lower jaw; however, this is not an absolute requirement and other arrangements are possible. Many times, only certain teeth are repositioned while other teeth will provide a base or anchor region for holding the aligner 200 in place as it applies the resilient repositioning force against the tooth or teeth to be repositioned.

The aligner 200 is formed from a sheet of a suitable elastomeric polymeric and more particularly, the aligner 200 is formed from a sheet of dental material. For example, the aligner can be formed a vacuum forming material that is used in the dental field and is available from a number of different commercial suppliers. In one embodiment, the aligner is formed of a vacuum forming material that is available is sheets of varying thicknesses from Henry Schein. For example, the sheets of vacuum forming material can come in thicknesses of 0.03", 0.035", 0.04", 0.06", 0.08", 0.10". It will be appreciated that that these sheet thicknesses are substantially greater than the 0.02" thickness of the material that is used to form the dental appliances offered from other manufacturers, and as such are more rigid and so they are able to impact a greater movement of teeth than possible using a thinner aligner such as in the Invisalign® system.

As described in detail below, the aligner 200 is intended to be worn over teeth without for wires or other attachment means being used and instead, the aligner 200 is constructed to hold the aligner 200 in place over the teeth without such external assistance.

Figure 3:
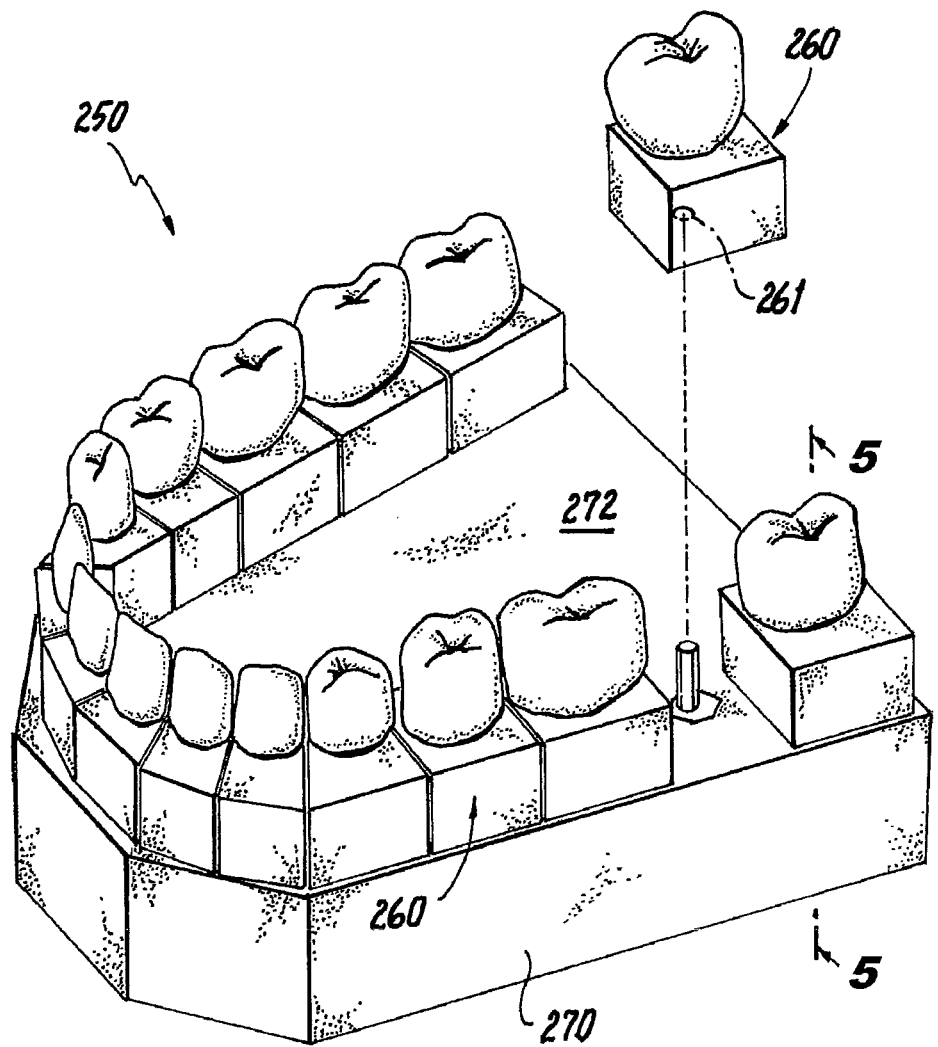
FIG. 3 is a perspective view of a dental model in accordance with the present invention showing a tooth die portion and a base portion in an assembled state with one dowel pin and tooth die being exploded.
Figures 4, 5:
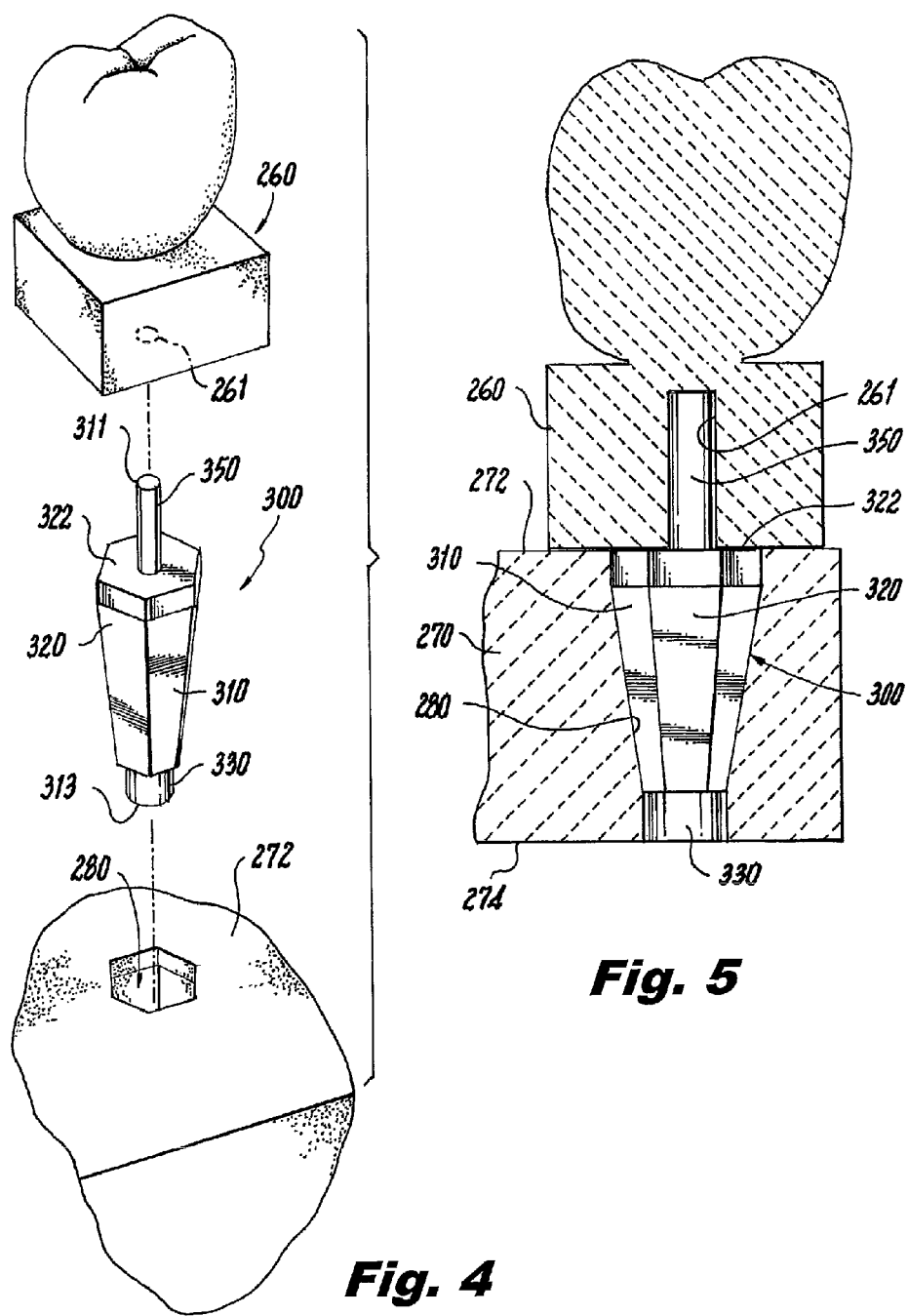
FIG. 4 is an enlarged exploded perspective view of the base portion, pin and tooth die.
FIG. 5 is a cross-sectional view taken along the line 5-5 of FIG. 3 of the base portion, pin and tooth die in the assembled state.

Now referring to FIGS. 3-5, an exemplary system and method of the present invention are shown.

In accordance with one embodiment of the present invention, a dental impression of the patient's teeth is first formed. As is known in the art, a dental impression is an accurate representation of part or all of a person's dentition and other areas of the mouth. From an imprint of a person's teeth and gums in wax or plaster, a dental impression forms a "negative" of those teeth and gums. The negative is then used to make a cast or model 250 of the dentition, which is also called a die and represents a positive replica of the tooth or teeth. An exemplary model 250 is shown in FIG. 3. The impression is carried out by placing a viscous liquid material into the mouth usually in a customized tray. The material then sets to become an elastic solid and when removed from the mouth retains the shape of the teeth. Common materials used for dental impression are sodium alginate, polyether and silicones (both condensation-cured silicones and addition-cured silicones, such as polyvinyl siloxane.

After forming the model 250 of the patient's teeth in the initial tooth arrangement, it is often desirable and typically necessary to separate one tooth die 260 from the remainder of the model of the patient's mouth. Any number of conventional techniques can be used to separate one tooth die 260 from the remainder of the model 250. For example, a cutting element can be used to separate each tooth die and in particular, the cutting element can be in the form of a mechanical cutting device, such as a saw, or it can be in the form of a laser that makes precise cuts. In order to permit the separated tooth die 260 to be replaced in its original relative position and orientation, the tooth dies 260 are provided with a dowel pin.

In accordance with the present invention, a device is used to form one or more openings 261 in an underside of the tooth die in order to allow coupling of the dowel pin to the tooth die (not shown). For example, a pin indexing or pinsetter device can be used to locate dowel pin openings. As is known, the pinsetter device offers precision die pinning featuring a laser light beam indicator for easier, more accurate dowel pin location. One exemplary pinsetting machine is commercially available from Coltene/Whaledent under the trade name Pindex Mark II Laser. The pinsetter device is thus used in the model and die fabrication process of the present invention and includes a small laser beak that makes drill hole positioning more accurate. It will thus be appreciated that the Pindex machine or the like is used to precisely drill holes in the model/die that permit each separated tooth die to be removed and replaced relative to the remaining part of the model.

The model 250 also includes a base 270 to which the tooth dies are removably coupled by means of dowel pin 300. The base 270 has a top planar surface 272 and a bottom planar surface 274 so that it can rest on a support surface, such as a table or the like. The base 270 includes a plurality of openings 280 that are formed generally about the perimeter of the base 270. The openings 280 are thus configured to correspond to the dies 260 and permit mating between the dies 260 and the base 270.

The openings 280 can be formed to have any number of different shapes as described herein so long as the dowel pins 300 have complementary shapes to allow insertion of the pins 300 within the openings 280. The number of openings 280 preferably (although is not limited to) corresponds to the number of dies 260. In one embodiment, the opening 280 has a non-circular shape to prevent free rotation of the pin 300 within the opening 280. In other words, it is preferred that the opening 280 is multi-sided so as to prevent the free, easy rotation of the pin 300. In other words, the opening 280 can have a polygonal shape. For example, the opening 280 can have the following shapes: triangle, pentagon, hexagon, etc. In addition, as will be appreciated below, the opening 280 can have a tapered shape to accommodate a tapered pin 300 and farther restrict movement of the pin 300 within the opening 280. In the illustrated embodiment, the opening 280 has an inwardly tapered construction in that the open end of the opening 280 has a greater width than the closed end of the opening 280.

The base 270 is formed using conventional techniques and once the openings 280 are determined, the base 270 is formed around molding elements (such as pins) that are used to form the openings 280. In this manner, the base 270 is complementary to the tooth dies 260 in that the pins 300 that are coupled to the tooth die 260 are received within complementary openings 280 formed in the base 270. In this manner, the tooth dies 260 can be returned to the base 270 and all the tooth dies 260 are maintained in their proper position despite being cut and being separate from adjacent tooth dies 260. FIG. 3 shows the base 270 containing a predetermined number of conventional openings 280 as well tooth dies 260 that are made in accordance with the present invention as discussed below.

FIGS. 3-5 show one exemplary pin 300. The pin 300 is an elongated structure that has a first end 311 and an opposing second end 313 with the first end 311 being the end that is coupled to the tooth die 260 and the second end 313 being the end that is inserted into the base 270. It will be appreciated that in one embodiment, the first end 311 is merely received within the opening or bore formed in the underside of the tooth die 260. This allows the tooth die 260 to be easily attached to and removed from the pin 300 by simply placing the tooth die on the pin 300 and conversely, the user can simply lift the tooth die 260 off of the pin 300. The opening in the tooth die 260 can be sized so that a frictional type fit can be formed between the tooth die 260 and pin 300.

The pin 300 can be thought of as including at least two distinct sections, namely, a main body section 310 and a tooth anchor section (e.g., a post) 350 that extends outwardly from the main body section 310. The main body section 310 is the portion that is received within the opening 280. The main body section 310 thus preferably does not include a circular shape so as to prevent free rotation of the main body section 310 within the opening 280.

It will also be appreciated that the main body section 310 can have a shape described in commonly owned, U.S. patent application Ser. Nos. 12/612,794, filed Nov. 5, 2009, and 12/632,356, filed Dec. 7, 2009, each of which is hereby incorporated by reference in its entirety. The main body section 310 can thus have a round shape and/or include a gear type shape along its length providing the directional orientation of the pin 300. The pin can also be part of a sleeve/pin arrangement as disclosed in the above applications. Therefore, it will be appreciated that the main body section 310 is not limited to a particular design but instead can be formed to have any number of different shapes, including but not limited to oval, triangle, round gear shape, etc.

For example, the main body section 310 can be a multi-sided structure that mates with the complementary multi-sided opening 280 resulting in the main body section 310 being held in place with respect to rotation of the main body section 310 relative to the base 270. However, it will be appreciated that the main body section 310 can be inserted in multiple different positions within the base 270 due to the multi-side nature of the opening 280 and main body section 310. For example, if the opening 280 and main body section 310 each has a pentagonal shape, the main body section 310 can be placed in one of five positions within the base 270. This results from one side of the main body section 310 be capable of be placed adjacent and in facing relationship with one of five sides of the base 270 that define the opening 280. Therefore, the number of sides of the polygonal structure will dictate how many possible positions the main body section 310 can be inserted into the base 270. The importance of having the ability to initially insert the pin base 310 in one of a plurality of positions within the base 270 will be appreciated in view of the following discussion.

In the illustrated embodiment, the main body section 310 includes several different portions or regions and in particular, can include a main multi-sided portion 320 and a bottom portion 330. The bottom portion 330 can have a different shape compared to the portion 320 and can be constructed to provide a means for holding the pin 300 upright in a storage tray or container or the like. As described herein, the bottom portion 330 includes an access point to an internal mechanism within the pin 300 that allows for an optional controlled tilt of the pin 300.

In addition, as described in detail below, a custom dental plan for a patient will include a set of pins 300 and therefore, the pins 300 are typically placed in some type of storage tray or container that is unique to the patient. For example, the bottom portion 330 can have a circular shape and can include surface features, such as ribs or the like that permit the pin 300 to be more easily held upright in place. The opening 280 in the base 270 is shaped to allow reception of the bottom portion 330 as well as the multi-sided portion 320. As mentioned above, even if the bottom portion 320 has a circular shaped, rotation of the pin 300 in the opening 280 is prevented by the multi-sided portion 320 and the corresponding multi-sided nature of the opening 280. It will be appreciated that the bottom portion 320 can have any number of other shapes, including a polygonal shape.

The main multi-sided portion 320 has a top surface 322. Preferably, the top surface 322 is a planar surface. In addition, in one embodiment, the top planar surface 322 lies flush with the top surface 272 of the base 270 when the pin 300 is inserted into the opening 280 of the base 270. It will also be appreciated that in other embodiments the top surface 322 of the portion 320 can lie below the top surface 272 of the base 270. The top surface 322 of the portion 320 thus has a polygonal shape according to one embodiment with the tooth anchor section (post) 350 extending upwardly therefrom.

In accordance with the present invention, the plurality of pins 300 that are used to treat a single patient are constructed so that the position of the tooth anchor section (post) 350 relative to the top surface 322 is not fixed but rather varies depending upon the custom treatment plan that is developed for this patient. In other words for at least one pin 300 that is associated with the tooth die that includes the target tooth or teeth that are desired to be moved over time, the location of the tooth anchor section (post) 350 varies over the course of treatment. It will be appreciated that since the tooth die 260 is directly coupled to the tooth anchor section (post) 350, the change in the location of the tooth anchor section (post) 350 will be translated into a corresponding change in the position of the tooth mold die 260 relative to the base 270. Thus, by progressively altering the location of the tooth anchor section (post) 350 relative to and on the top surface 322 of the portion 320, the corresponding tooth die 260 is likewise progressively moved in a mirrored manner. In other words, if from one pin 300 (n) to the next pin 300 (n+1), the post is moved x distance, than the coupled tooth die 260 will likewise be moved x distance. It will be appreciated that in this embodiment, each pin 300 is placed in the same orientation within the opening 280. For example, if face A of the one pin 300 is placed adjacent face A of a side wall of the base that defines the opening 280, then when the next pin 300 is placed into the same opening 280, the face A of the next pin 300 is placed adjacent the face A of the base side wall. As will be described hereinafter, in some other embodiment, the relation of the face of the pin 300 and the face of the side wall of the opening 280 can likewise be changed over the course of inserting multiple different pins within the opening 280 and this provides the ability to incorporate another degree of movement of the tooth anchor section (post) 350 over the course of the treatment.

FIGS. 6(a)-6(h) show one set of pins 300 that have been manufactured and are customized for one patient based on the needs of this patient. As discussed herein, the construction of the main body section 310 does not vary from amongst the pins 300 that are included in the pin set. The only difference between each pin 300 within the set is the location of the tooth anchor section 350 relative to the main body section 310.

Figure 6A:
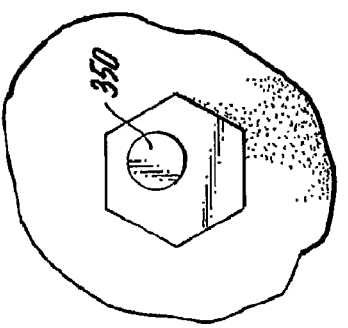
FIGS. 6(a)-6(h) are top plan view of a set of dowel pins showing successive, progressive linear movement of a tooth anchor portion (post) along a top surface of a main body portion of the pin.
Figure 6B:
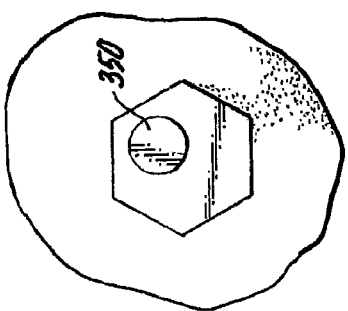
Figure 6C:
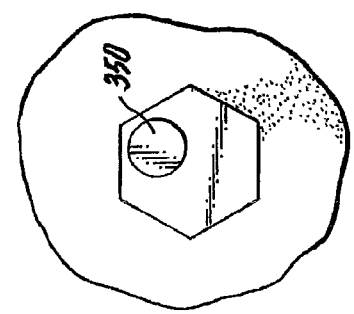
Figure 6D:
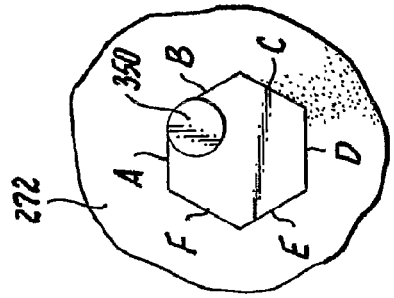
Figure 6E:
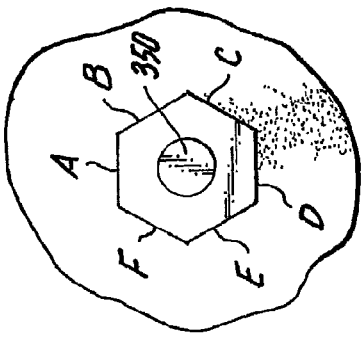
Figure 6F:
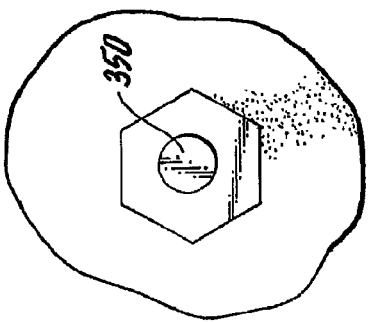
Figure 6G:
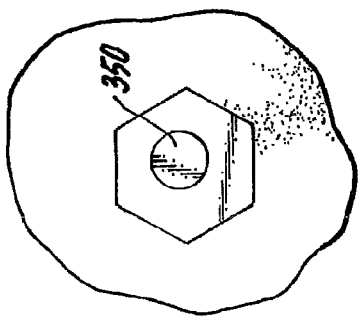
Figure 6H:
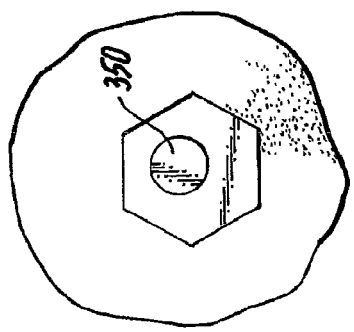
Figure 7D:
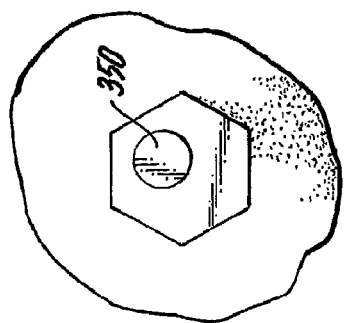
FIGS. 7(a)-7(h) are top plan view of a set of dowel pins showing successive, progressive complex movement (along two axes) of a tooth anchor portion (post) along a top surface of a main body portion of the pin.
Figure 7H:
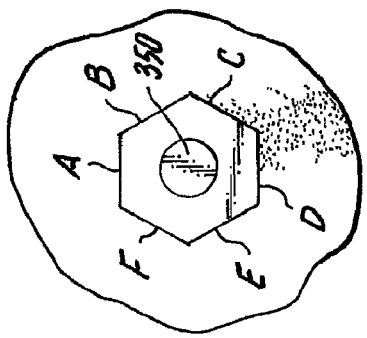
Figure 7C:
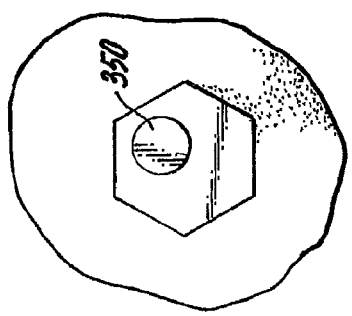
Figure 7G:
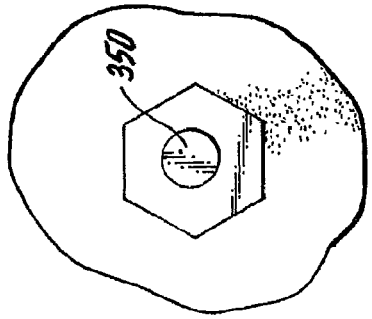
Figure 7B:
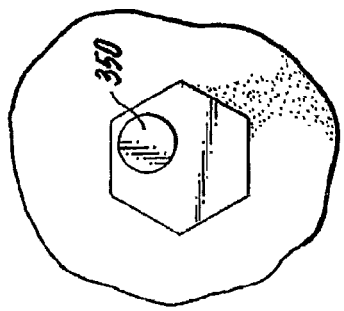
Figure 7F:
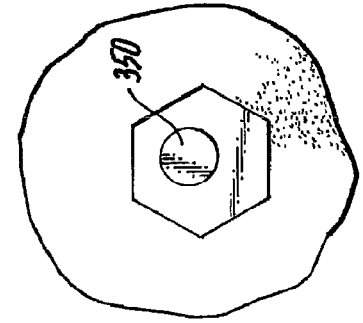
Figure 7A:
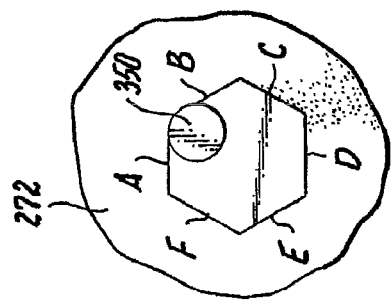
Figure 7E:
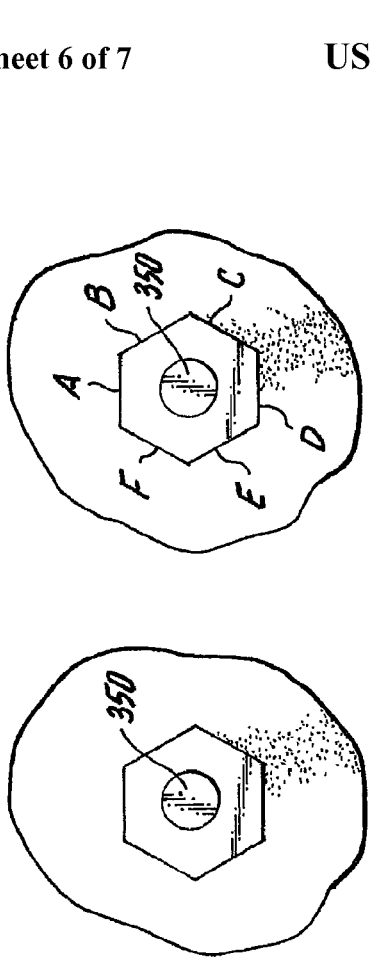

FIG. 6a shows a pentagonal shaped pin 300 and the multi-sided portion 320 includes sides or faces A, B, C, D, E and F. FIGS. 6a-6h show a more simple dental treatment plan in which one tooth of a patient needs to be moved generally linearly within the patient's mouth. In other words, it is desirable to move one tooth either left or right along the patient's jaw. For ease of example and illustration, this example does not include a consider of moving the patient's tooth along two or more axes but rather is limited to movement along a single axis to convey the basic principles of the present invention.

It will be appreciated that the initial starting point or location of the tooth anchor section (post) 350 relative to the top surface 322 can vary depending upon the precise needs of the patient and more specifically, the distance that is required to move the tooth from its current position to the target position. For example, if the patient's tooth needs to be moved 2 mm in one direction and the dentist has determined that 8 individual trays 200 are to be used for causing the incremental movement of the tooth, then each tray can correspond to a tooth movement of ¼ mm. The pin set of the present invention allows for complete customization since not only the number of pins 300 that are used over the treatment can be varied but also the incremental movement of the tooth die 260 from one setting to the next incremental setting can be varied. For example, in the above example, the incremental shifts of the tooth die 260 are even over the 8 individual trays 200 in that for each tray 200, there was a ¼ mm change in the position of the tooth die 260, which results in the ¼ mm change in the position of the patient's tooth. However, the incremental change in the location of the posts 350 between successive trays does not have to be the same across the entire sets of pins 300. For example, the tooth die 260 can be moved in increments of ¼ mm for the first 4 trays 200 and then the tooth die 260 can be moved ½ mm in an intermediate tray 200 before then being moved in increments of ¼ mm for the last successive trays 200. It will be appreciated that there are a vast number of different customized plans that can have uniform or non-uniform increments of change in the location of the post 350.

In FIGS. 6a-6h, the initial starting point of the post 350 is at or near one perimeter edge of the top surface 322 and the end point of the post 350 is at or close to the center of the top surface 322. However, this is merely one treatment plan that is designed to incrementally move a tooth from its initial position to a target position. The distance x between the tooth's initial position and the target position is mirrored in the movement of the post 350 in that the distance between the post 350 in the initial starting point and the end point is the same distance x. It will be appreciated that the starting point for the post 350 can be offset from the perimeter edge of the starting position or even be at or near the center of the top surface 322. It will also be appreciated that the maximum distance that post 350 can travel across the top surface 322 is defined by the shape and size of the top surface 322 and is likely defined by travel from one edge of the top surface 322 all the way across to the other edge of the top surface 322. In this embodiment, the post 350 thus is initially located near one edge of the top surface 322 and travels across the top surface 322 to an opposite edge thereof.

As mentioned above, it will also be appreciated that the post 350 can move in and along more than one axis across and relative to the top surface 322. For example, FIGS. 7(a)-7(h) show a complex movement of the post 350 across the top surface 322. In this embodiment, not only does the post 350 move in one direction (e.g., from a perimeter edge of the top surface 322 toward the center) but it also moves in another direction at the same time, e.g., toward another perimeter edge. In other words, the movement is not merely linear along the top surface 322 but rather incorporates movement in another direction as well. For example and as shown in the successive movements of the pin 350 across the top surface 322, the post 350 can move in an arcuate manner in that there is movement along two axes, namely, X and Y axes. In this manner, the corresponding tooth die 260 that is attached to the post 350 moves in the same manner to allow the successive trays 200 to be formed.

It will therefore be appreciated that once the dentist knows the exact treatment plan and knows not only the distance and direction that a particular tooth or teeth need to be moved, the dentist can then chart out a course of treatment. Other considerations will be the total length of time that is allocated for treatment (e.g., how many trays 200 will be used over how long a period of time), as well as patient considerations.

Such treatment plan can be generated with the assistance of computer software.

Figures 8, 9:
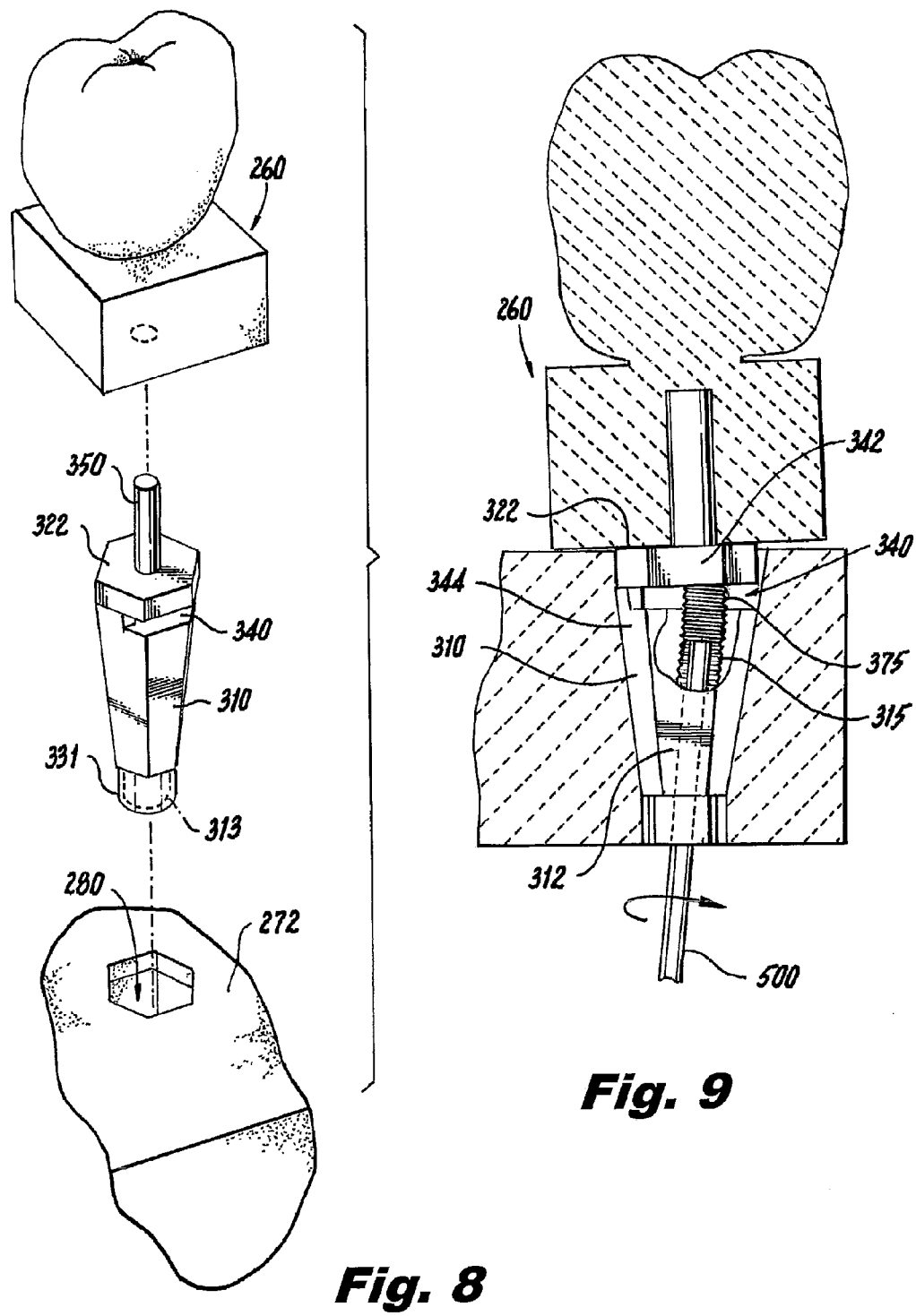
FIG. 8 is a perspective view of an alternative pin that include an internal tilt mechanism to allow the tooth anchor portion to tilt.
FIG. 9 is a cross-sectional view of the alternative pin of FIG. 8.

In yet another embodiment, the pin 300 is also preferably adjustable as shown in FIGS. 8 and 9. As described above with reference to the set of pins 300 with varying post position, the adjustable dowel pin assembly 300 is intended to be used with a tooth die 260 (FIG. 3) that is associated with one or more teeth that are to be incrementally moved during the course of treatment.

The pin 300 is likewise an elongated structure that has a first end 311 and an opposing second end 313 with the first end 311 being the end that is fixedly coupled to the tooth die and the second end 313 being the end that is inserted into the base 270.

The tooth anchor section (post) 350 represents the portion of the pin 300 that is inserted into the drill hole formed in the underside of the tooth die 260 and therefore the tooth anchor section 350 is received within the tooth die and fixedly attached thereto. The tooth anchor section 350 can have a contoured or modified outer surface to assist in fixedly attaching the pin 300 to the tooth die. For example, the outer surface can be serrated or can have other surface modifying structures. In the illustrated embodiment, the outer surface is a ribbed surface formed of a plurality of vertically oriented ribs (e.g., ribs that run longitudinally along the length of the tooth anchor section 350.

The tooth anchor section 350 can have any number of different shapes; however, the shape of the tooth anchor section 350 is complementary to the shape of the drill hole since the tooth anchor section 350 is received within the drill hole. In the illustrated embodiment, the tooth anchor section 350 has a cylindrical shape.

The anchor section 350 extends beyond the main body section 310 and therefore represents a post or the like. The anchor section 350 is preferably a solid structure to increase the integrity and strength of the connection between the pin 310 and the tooth die.

The main body section 310 is not a solid structure but rather the main body section 310 has a bore 312 formed therein. The bore 312 can be drilled in along the axis of the main body of the pin or off centered or on an angle. In the illustrated embodiment, the main body section 310 has a pentagonal shape. In addition, the width (diameter) of the main body section 310 is greater than the width (diameter) of the tooth anchor section 350. As a result, a shoulder is formed between one end of the main body section 310 and the tooth anchor section 350. The shoulder has an annular shape. Optionally, the tooth anchor section 350 can be bonded as by an epoxy or cement to a tooth with the bond being between the tooth die 260 and the surface 322.

In accordance with the present invention, the main body section 310 has a living hinge 340 formed therein. The living hinge 340 is located proximate the end of the main body section 310 that interfaces with the tooth anchor section 350. The living hinge 340 is thus in the form of a cut or slot that is formed in main body section 310. This slot partitions the main body section 310 into a first part 342 that is located above the slot and extends toward the tooth anchor section 350 and a second part 344 that is located below the slot and extends toward the end 313. The living hinge 340 allows for relative movement between the first and second parts 342, 344. The slot is thus a wedged shaped cut.

The cut or slot that is formed in main body section 310 is, according to one embodiment, not prefabricated (preformed) into the main body section 310 but rather, when tilting motion of the post 350 is needed or desired, the slot can be cut into the main body section 330 using conventional tools. The pin 300 can thus include the internal tilt mechanism that is incorporated therein for tilting the post 350; however, in the event that a tilt motion is not desired or needed, the slot is not cut into the main body section 310.

The main body section 310 has the bore 312 formed therein. The bore 312 extends along the longitudinal axis of the main body section 310. The bore 312 is open at one end of the pin 300, while the other end of the bore 312 forms an entrance into the slot. In other words, the bore 312 is open and accessible at the end of the pin 300 that includes the bottom 330. The bore 312 itself can have any number of different shapes and in the illustrated embodiment, the bore 312 has a circular or hexagonal shape. At least a portion 315 of the bore 312 is in the form of a threaded bore. In other words, a section 315 of the bore 312 is threaded. The section 335 is formed at one end of the bore 332 and in particular, the section 335 is formed at the end of the bore 332 that forms an entrance into the slot 342. The bore 312 can be formed at an angle as shown or it can be formed perpendicular to the top surface 322.

The main body section 310 also includes an urging member 375 that is located within the bore 312 and in designed to travel along the threaded section 315. In one embodiment, the urging member 375 is in the form of an urging screw that is located within the bore. The urging screw 375 has external threads that are complementary to the threaded section 315 and therefore, the urging screw 375 threadingly mates with and travels along the threaded section. The urging screw 375 thus has a complementary shape relative to the bore 312 and in particular, the threaded section 315 and therefore, in one embodiment, the urging screw 375 has a circular or hexagonal shape.

In the embodiment of FIGS. 8 and 9, it is desirable, although not mandatory, to have a bottom cap 331 that closes off the bore 312 at the end 313. The bottom cap 331 is designed to fit over and be held on (e.g., frictionally held) on the bottom section 330. The bottom cap 331 thus prevents unwanted foreign debris from entering the bore 312. When used, the bottom cap 331 is preferably flush or slightly countersunk relative to the bottom surface of the base 270.

The operation of the optional tilting action of the pin 300, is now described. Once the tooth anchor section 350 is fixedly attached to the tooth die, the tooth die can be moved in a number of different directions by manipulation of the pin 300. For example, if it desired to move the tooth die in one or more directions indicated (e.g., a forward/rearward movement of the tooth), the pin 300 is fixedly attached to the tooth die such that the living hinge 340 opens in this same direction as the desired movement of the tooth die. If the tooth die is desired to move in left-to-right movement, then the pin 300 is simply attached to the tooth die with the living hinge 340 opening in this left-to-right direction. It will therefore be appreciated that the tooth die can be moved in any number of different directions to accommodate the tooth movements that are normally encountered in orthodontic treatments. FIGS. 8 and 9 shows two different orientations of the pin 300 relative to the tooth die 260. In particular, FIG. 8 shows the living hinge 340 in an unopened state, while FIG. 9 shows the hinge 340 in an open position. Advantageously, after adjustment of the tooth die, it remains in the new position which allows a new aligner to be created.

A tool 500 is provided for engaging the urging screw 375. For example, a small Allen wrench type tool can be provided for insertion into the bore 312 and for mating with the urging screw 375. Rotation of the tool 500 causes rotation of the urging screw 375 resulting in the urging screw traveling along the threaded section 315 (whether the urging screw is driven toward or away from the tooth die depends on which direction the tool is rotated). To cause movement of the tooth die, the urging screw 375 is driven along the threaded section 315 until the urging screw 375 enters the slot of the living hinge 340 and comes into contact with the underside of the first part 342 that is located above the slot. It will be appreciated that continued movement of the urging screw 375 caused an upward force to be applied to the first part 342 and since the first part 342 is connected to the second part 344 by means of the living hinge 340, the first part 342 pivots about the living hinge 340 resulting in a pivoting of the tooth die that is attached to the tooth anchor 350 (which is directly connected to the first part 342).

The degree to which the urging screw 375 is driven into the slot depends upon the degree of pivoting in the tooth die that is desired. Thus, depending upon the degree of intended movement of the tooth die, the urging screw is driven a certain amount into contact with the In other words, the angle that the hinge 340 opens correlates to the degree of movement of the tooth die. If the tooth die is only intended to pivot a small amount as in the case with a patient that only needs minor correction of the tooth position, then the living hinge 340 is only opened a small amount. Conversely, if the patient's tooth requires more severe movement, then the urging screw is driven to a greater degree to cause the living hinge 340 to open to a greater degree. The degree that the hinge 340 opens is controlled with precision by using the tool 500 to cause the urging screw to open the hinge 340 to the desired degree. If the hinge 340 is opened too much, the orthodontist simply has to rotate the tool in the opposite direction to cause the urging screw to back away from the first part 342.

As a result, the tooth die 260 can be adjusted according to a number of different degrees of freedom using the pin 300 of the present invention in place of a conventional dowel pin.

Thus, the set of pins 300 of the present invention can be customized so that the corresponding tooth die 260 can be moved in a number of different directions in order to create the desired trays 200. The tooth dies 260 can be moved along two axes by successive movement of the post 350, while the tooth die 260 can likewise be moved along yet another axis, e.g., z-direction, by means of the tilt mechanism.

It will be appreciated that the pin 300 can be formed according to conventional techniques, such as injection molding using molds. When injection molding is used, the urging member (urging screw) 375 is disposed within the mold and the pin structure is formed therearound. As a result, the urging member 375 is located within the bore 312: In addition, the tool 500 can be disposed within the mold so as to form a lower portion of the bore 312.

As a result of incorporating the pin 300 into one or more of the tooth dies 260, the tooth dies 260 that form a part of the model can be manually manipulated by the orthodontist to suggest and formulate an orthodontic treatment plan for a particular patient. As described above, by first setting the living hinge 340 in the correct position relative to the tooth die 260, the tooth die 260 can be moved in increments until the tooth die assumes its final, desired position.

It will also be appreciated that when the tilt mechanism is included within the pin 300, successive aligners can be fabricated without requiring movement of the location of the tooth anchor section 350. In other words, successive aligners can be fabricated using successive tooth die models with the only difference being that the pin 300 is tilted while the location anchor section 350 remains stationary. However, if a tilt action of the tooth die 260 is desired, it will be appreciated that the tilt action can be incorporated in a pin 300 in which the tooth anchor section 350 has also been changed. Thus, a new aligner does not have to be necessarily fabricated when the only movement of the tooth die 260 is a tilt movement as opposed to the tooth die 260 being moved along the two axes of the planar top surface 322.

The use of the present model for the formation of the plurality of aligners to cause the patient's teeth to move from the initial tooth arrangement to the final tooth arrangement is now described. More specifically, the orthodontist has a great amount of discretion in the customization of the orthodontic treatment plan for a particular patient since the orthodontist can make proposed adjustments to one or more tooth dies by manipulating the respective pin 300, including altering the location of the tooth anchor portion, to cause the desired movements of the respective tooth dies.

There is a significant cost savings using the present invention since the adjustments that are made using the assembly of the present invention can be made by conventional heat-forming technique without computer controlled machines on site. The better interaction with a patient by showing the patient corrective ships steps on a material 3-D model instead of a computer screen. In other words, the personal dentist can work with his or her own patient in developing and personally illustrating the proposed treatment plan. This is a significant advantage since the patient will better appreciate the course of treatment when it is shown before their very eyes in a physical 3-D model. Planning every next step based on a real progress taking into account the actual patient's response to the adjustments, etc., as opposed to charter an entire course of treatment as is done in the prior art systems. Since the system and method of the present invention is customizable, the course of treatment can be changed mid treatment if the patient is making more or less progress than anticipated.

After moving the respective tooth dies from the initial tooth arrangement to a first tooth arrangement, the model is then used in the formation of a unique aligner. To form the aligner, the model is inserted into a vacuum forming system. The vacuum forming system has a compartment that has a platform that receives the model. Surrounding the model is a plurality of vacuum apertures or the like which cause a vacuum to be established in the compartment. The platform on which the model rests is often called a vacuum plate. The system includes a heating unit that includes a heating element. The heating unit is typically rotatable and is spaced from the platform. The vacuum forming system has a frame that includes the platform and has a hinged frame part that receives a sheet of vacuum forming material. The hinged frame part is closed and secured with a frame latch, thereby positioning the sheet of vacuum forming material over the model. The heating unit is then swung into position squarely over the sheet of vacuum forming material and at this time, the vacuum is on. The plastic vacuum forming material heats quickly and begins to soften and the vacuum forming material flows over the model (tooth dies).

A suitable vacuum forming system is commercially available from Buffalo Dental under the trade name Sta-Vac II. The Sta-Vac II uses a heating element other than a laser and therefore, unlike the Invisalign® system, vacuum forming materials of greater thickness can be used. As previously mentioned, the Invisalign® system uses a laser light vacuum forming system and therefore, a thin sheet of vacuum forming material is required to be used due to the heating properties and capabilities of the laser.

The vacuum forming system is then turned off and after a sufficient cooling period, the formed aligner is removed and can be cut to remove fringe material, etc., thereby leaving behind an aligner (polymeric shell) that is fabricated for placement over the patient's teeth. As described above, the aligner applied a resilient repositioning force against the tooth or teeth to be repositioned.

The patient's teeth are repositioned from their initial tooth arrangement to an intermediate and/or final tooth arrangement by placing a series of incremental aligners over the patient's teeth. To form the next aligner for use by the patient, the orthodontist simply manually manipulates the tooth die(s) that requires further repositioning and thereby causes adjustment of the respective pin 300. Once the proper tooth arrangement is achieved, the orthodontist repeats the process and places the adjusted model into the vacuum forming system. The vacuum forming system is operated, as described above, a new aligner is formed.

The above process is repeated until the desired number of aligners is formed. Unlike the conventional processes, a treatment plan using the aligners of the present invention is more customizable and the length of treatment can be reduced since the thicker aligners can be used and therefore, more aggressive incremental changes can be realized.

It will be appreciated that the pin 300 according to the present invention permits the model of the patient's teeth to be interactive in that the orthodontist can manipulate individual tooth dies until the tooth die assumes a desired tooth arrangement that includes an incremental change relative to the prior tooth arrangement. The degree and magnitude of the incremental tooth change is left up to the individual orthodontist. As a result; the orthodontist can customize and tailor the treatment plan to a particular patient and not be limited by parameters, such as the thickness of the aligner due to the starting thickness of the sheet of vacuum forming material.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A dental model kit comprising:
    a base;
    at least one tooth die;
    a set of dowel pins for successive use with the at least one tooth die for incrementally moving at least one tooth of a patient from an initial position to a final position, each dowel pin including:
        an upstanding tooth anchor section that is configured to be fixedly attached to the at least one tooth die; and
        a main body section having a top surface from which the tooth anchor section extends and on which the at least one tooth die rests, the main body section for removable reception within a fixed opening formed in the base of the dental model kit, wherein the tooth anchor section is integrally formed with the main body section;
    wherein for each tooth die, there are a plurality of corresponding dowel pins of the set of dowel pins for specific use with the respective tooth die, the plurality of corresponding dowel pins including at least;
    a first dowel pin in which the tooth anchor section thereof is located at a first location relative to the top surface of the respective main body section and a second dowel pin in which the tooth anchor section thereof is located at a second location relative to the top surface of the respective main body section, the second location being different than the first location, wherein the main body sections of the first and second dowel pins have the same construction and shape to allow successive reception into the same fixed opening formed in the base, wherein the tooth anchor sections of the plurality of dowel pins are formed at different locations relative to the top surfaces of the respective main body sections such that successive use of the plurality of dowel pins is translated into successive movement of the tooth die that is attached thereto and is intended to be moved both in a desired direction and a desired distance for incrementally moving the at least one tooth of the patient from the initial position to the final position.

2. The kit of claim 1, wherein, for each dowel pin, the tooth anchor section comprises a post; wherein the tooth anchor section of the first dowel pin in the first location and the tooth anchor section of the second dowel pin in the second location extend at the same angle relative to their respective main body sections.

3. The kit of claim 1, wherein, for each dowel pin, the tooth anchor section comprises a post; wherein the difference in position of the tooth anchor section of the first dowel in in the first location compared to the tooth anchor section of the second dowel in in the second location is measured along two axes.

4. The kit of claim 1, wherein the first location of the tooth anchor section of the first dowel in is closer to a peripheral top edge of the respective main body section compared to the second location of the tooth anchor section of the second dowel pin.

5. The kit of claim 1, wherein the second location of the tooth anchor section of the second dowel pin is closer to a peripheral top edge of the respective main body section compared to the first location of the tooth anchor section of the first dowel pin.

6. The kit of claim 1, wherein, for each dowel pin, the main body section has a tapered shape.

7. The kit of claim 1, wherein, for each dowel pin, the main body section comprises a polygonal shape.

8. The kit of claim 1, wherein, for each dowel pin, the main body section has a bore formed therein and open at one end of the pin, the main body section further having a slot that defines a living hinge formed therein that partitions the main body section into an upper pivotable portion that pivots about the hinge and a lower portion, wherein a section of the bore is threaded and the main body section includes an urging member that travels along the threaded bore section and can be driven into contact with the pivotable portion of the main body section, the bore forming an entrance into the slot that defines the living hinge to permit the urging member to be driven into contact with the pivotable portion.

9. The kit of claim 8, wherein, for each dowel pin, the urging member comprises a screw that has external threads that are complementary to the threaded bore section.

10. A manually adjustable physical 3-D model that has a plurality of tooth dies, wherein at least one of the plurality of tooth dies can be selectively adjusted to a new position to allow formation of an aligner that is intended to be worn on teeth of the patient for incrementally moving at least one tooth of a patient from an initial position to a final position; the model comprising:
    a first model part that is formed of the plurality of tooth dies;
    a second model part complementary to the first model part and being in the form of a base that supports the plurality of tooth dies, wherein the base has a plurality of fixed openings formed therein at fixed locations; and
    a set of dowel pins, each dowel pin for use with one tooth die of the plurality of tooth dies that is intended to be adjusted, each dowel pin including:
        an upstanding tooth anchor section that is configured to be fixedly attached to the tooth die to be adjusted; and
        a main body section having a top surface from which the tooth anchor section extends and on which the at least one tooth die rests, the main body section for reception within one of the openings formed in the base;
    wherein for each tooth die, there are a plurality of corresponding dowel pins of the set of dowel pins for specific use with one of the plurality of tooth dies, the plurality of corresponding dowel pins including at least:
        a first dowel pin in which the tooth anchor section thereof is located at a first location relative to the top surface of the respective main body section and a second dowel pin in which the tooth anchor section thereof is located at a second location relative to the top surface of the respective main body section, the second location being different than the first location, wherein the main body sections of the first and second dowel pins have the same construction and shape to allow successive reception into the same one of the fixed openings formed in the base, wherein the tooth anchor sections of the plurality of dowel pins are formed at different locations relative to the top surfaces of the respective main body sections such that successive use of the plurality of dowel pins is translated into successive movement of the tooth die that is attached thereto and is intended to be moved both in a desired direction and a desired distance for incrementally moving the at least one tooth of the patient from the initial position to the final position.

11. The kit of claim 10, wherein, for each dowel pin, the tooth anchor section comprises a post; wherein the tooth anchor section of the first dowel pin in the first location and the tooth anchor section of the second dowel in in the second location extend at the same angle relative to their respective main body sections.

12. The kit of claim 10, wherein, for each dowel pin, the tooth anchor section comprises a post; wherein the difference in position of the tooth anchor section of the first dowel in in the first location compared to the tooth anchor section of the second dowel in in the second location is measured along two axes.

13. The kit of claim 10, wherein the first location of the tooth anchor section of the first dowel pin is closer to a peripheral top edge of the respective main body section compared to the second location of the tooth anchor section of the second dowel pin.

14. The kit of claim 10, wherein the second location of the tooth anchor section of the second dowel pin is closer to a peripheral top edge of the respective main body section compared to the first location of the tooth anchor section of the first dowel pin.

15. The model of claim 10, wherein, for each dowel pin, the main body section has a tapered shape.

16. The model of claim 10, wherein, for each dowel pin, the main body section comprises a polygonal shape.

17. The model of claim 10, wherein, for each dowel pin, the main body section has a bore formed therein and open at one end of the pin, the main body section further having a slot that defines a living hinge formed therein that partitions the main body section into an upper pivotable portion that pivots about the hinge and a lower portion, wherein a section of the bore is threaded and the main body section includes an urging member that travels along the threaded bore section and can be driven into contact with the pivotable portion of the main body section, the bore forming an entrance into the slot that defines the living hinge to permit the urging member to be driven into contact with the pivotable portion.

18. The model of claim 17, wherein, for each dowel pin, the urging member comprises a screw that has external threads that are complementary to the threaded bore section.

\* \* \* \* \*